United States Patent [19]

Dowling

[11] Patent Number: 4,644,330

[45] Date of Patent: Feb. 17, 1987

[54] ANTI-SNORING DEVICE

[76] Inventor: Anthony R. Dowling, 7 Wentworth Road, Vaucluse, New South Wales 2030, Australia

[21] Appl. No.: 658,492

[22] Filed: Oct. 9, 1984

[30] Foreign Application Priority Data

Oct. 11, 1983 [AU] Australia .............................. PG1776

[51] Int. Cl.⁴ ............................................ G08B 23/00
[52] U.S. Cl. ...................................... 340/575; 340/573
[58] Field of Search ..................... 340/575, 576, 573; 180/272

[56] References Cited

U.S. PATENT DOCUMENTS

| | | | |
|---|---|---|---|
| 3,089,130 | 5/1963 | Wilson | 340/575 |
| 3,998,209 | 12/1976 | Macvaugh | 128/1 R |
| 4,220,142 | 9/1980 | Rosen et al. | 340/575 X |
| 4,297,685 | 10/1981 | Brainard, II | 340/575 |

FOREIGN PATENT DOCUMENTS 83286403 2/1984 Fed. Rep. of Germany .
3322571 4/1984 Fed. Rep. of Germany .

Primary Examiner—James L. Rowland
Assistant Examiner—Jeffery A. Hofsass
Attorney, Agent, or Firm—Ladas & Parry

[57] ABSTRACT

A compact self-contained electronic anti-snoring device is adapted to be worn in the outer ear or attached thereto. It comprises a miniature microphone for detecting snoring sounds and means responsive to the detection of snoring sounds for generating an aversive audio signal. The aversive audio stimulus is emitted via a speaker in the user's ear. Preferably, a combined microphone/speaker is used and the snoring sounds are detected via the auditory canal. Means are also provided to vary the amplitude and duration of the audio stimulus with successive snores to obviate habituation. A counter is also provided to record the number of snores during a sleeping period and provide an indication of the effectiveness of the device.

9 Claims, 4 Drawing Figures

ANTI-SNORING DEVICE

The present invention relates to an electronic anti-snoring device. In particular, the invention is directed to a behavioural conditioning device which detects the sound of a snore and provides an aversive stimulus to the sleeper to condition him to sleep without snoring.

Early attempts to eliminate snoring used mechanical devices which were designed to fit into the snorer's mouth or around his chin to physically prevent snoring. Examples of such devices can be found in British Pat. No. 1,248,474 and U.S. Pat. Nos. 3,434,470; 3,312,217 and 3,132,647. These mechanical devices were not popularly accepted since they suffered from the disadvantage that they were uncomfortable to wear and interfered with the user's sleep. Furthermore, they were of limited success in preventing snoring, and snoring returned when use of the devices was discontinued.

A later generation of anti-snoring devices worked on the principle of detecting a snore electronically and making the snorer conscious of the fact that he had snored. U.S. Pat. No. 2,999,232 discloses a device adapted to be worn by a sleeper and to provide an alarm automatically when the person's mouth opens, whereby the device causes the sleeper to become conscious of the fact that he has lost control of his mandible. The device of U.S. Pat. No. 3,480,010 consists of a neck band worn by the sleeper which comprises a circuit to detect a snore and to impart a high voltage shock to the sleeper to condition him against snoring. Similarly, German Pat. No. DE 3,018,336 and U.K. Patent Application No. 2,103,807 disclose apparatus responsive to snoring sounds to impart a stimulus voltage to the snorer.

These devices suffer from the disadvantage that their use can result in nervous injury to the user by continually waking him up or giving him electric shocks. It should be remembered that the snoring does not annoy the snorer, but his partner. Thus, the snorer will be reluctant to use a device which is uncomfortable or painful when he is not malaffected by the snoring. Further, it is clearly inadvisable for a device to incorporate an alarm or other stimulus which is likely to disturb the snorer's partner. Both considerations are taken into account by the present invention.

The search for an improved anti-snoring device has resulted in some ingenious, but impracticable devices. For example, U.S. Pat. No. 3,089,130 discloses apparatus which senses a person's snoring and awakens the sleeper by shaking his pillow. Not only is the sleeper awakened by his snoring but also the invention requires a complex arrangement of electro-mechanical devices. The device of U.S. Pat. No. 3,696,377 comprises a tape recorder which is actuated by the sound of snoring to play back a pre-recorded message to the sleeper via an ear plug. One major disadvantage of the known device is that as the ear plug is connected to the tape recorder by a cord, the sleeper is likely to become entangled in the cord or the ear plug is likely to become dislodged if the sleeper tosses and turns during the night and the device therefore becomes ineffective. Another anti-snoring device which uses behavioural conditioning is disclosed in U.S. Pat. No. 4,220,142. This device incorporates a memory and counter and visual display to register and report the number of times the sleeper snores during the night.

In the known devices, the means which sense the sound of snoring do not discriminate between snores and other sounds. Thus, the stimulus to the sleeper could be activated by background noises of sufficient loudness. As many other types of noise can occur in a bedroom during sleep this lack of discrimination is considered a major flaw. The nature of snoring sounds was discussed in U.S. Pat. No. 3,998,209. It was recognised that snore sounds comprise a strong component of frequencies concentrated in a narrow band and it was suggested that it would be feasible to use a narrow band-pass filter to enable the sound detector to selectively respond to those frequencies. However snore sounds in fact cover a wide frequency range and a single narrow band filter may not be effective as a discriminator for different users.

It is an object of the present invention to provide a compact self-contained anti-snoring device which can be worn comfortably in the ear of the sleeper and which provides an aversive but not dangerous stimulus to the wearer.

According to the present invention, there is disclosed a compact self-contained electronic anti-snoring device adapted to be worn in or mounted to the outer ear of the user, said device comprising receiving means adjacent to the ear for detecting snoring sounds of the user, signal generating means connected to the output of said receiving means and responsive to detection of the snoring sounds for generating an aversive audio signal, and speaker means connected to said signal generating means and adapted to be worn in the outer ear of the user.

The anti-snoring device of the present invention is a compact self-contained unit which is mounted on the ear of the user, and preferably it fits entirely in the outer ear. Unlike the prior art arrangements, there are no wires or straps in which the user can become entangled. The device is self-powered and therefore can be used anywhere, e.g. on aircraft, camping etc. Moreover, the device is comfortable to wear. The aversive stimulus given to the snorer is an irritating sound. No dangerous electrical shock is imparted and no high powered voltage generator is required as in the prior art circuits. Since the speaker means are worn in the outer ear of the user, the stimulus is entirely personal to the user and does not disturb the snorer's partner.

Preferably, the receiving means comprises a microphone which also fits in the outer ear and detects the snoring sounds via the head and auditory canal of the ear. Thus, the microphone is in constant spatial relationship to the source of the snores, as opposed to prior art devices in which the microphone is not attached to the head. By placing the microphone in the ear, the snores can be detected even when the device is pressed firmly on the pillow. The ear provides a degree of shielding from noises not passing via the auditory canal and thus, the device will not be accidentally triggered by the snoring of the user's partner.

Typically, a combined microphone/speaker is used. This reduces the size of the device and its cost, and makes the device more comfortable to wear.

Typically, the audio stimulus is of sufficient amplitude to be irritating to the sleeper but not necessarily so loud as to fully awaken him. Preferably, the amplitude and/or duration of the audio stimulus increases with the number of successive snores in a time bracket thus automatically increasing its aversiveness. By automatically increasing the aversiveness of the stimulus any snorer will receive just the right amount of stimulus to disrupt snoring in all circumstances without the need to set the level manually. This facility also counteracts the natural tendency to habituate (or learn to ignore) the stimulus. Thus, the sleeper either subconsciously or consciously becomes aware of the aversive stimulus each time he snores and his behavious is conditioned to reduce and eventually eliminate snoring.

An optional feature of the present invention is the provision of a random generator to vary the manner in which the intensity and duration of the audio stimulus is varied with increasing snores. This feature is an additional safeguard against habituation to the audio stimulus.

Preferably, counter means are provided to count the number of snores during the night. This number is encoded and is able to be replayed via the speaker in a detectable form to enable the user to monitor the effectiveness of the device and his progress.

As a safety feature, a cut out can be provided to terminate operation of the device if more than a preset number of snores are detected during a particular period of time. This would be an indication that the user is not responding effectively to the stimulus, and the audio stimulus is no longer applied to avoid the possibility of ear injury.

Notwithstanding other forms of the invention, a preferred embodiment thereof will now be described with reference to the accompanying drawings, in which.

Figure 1:
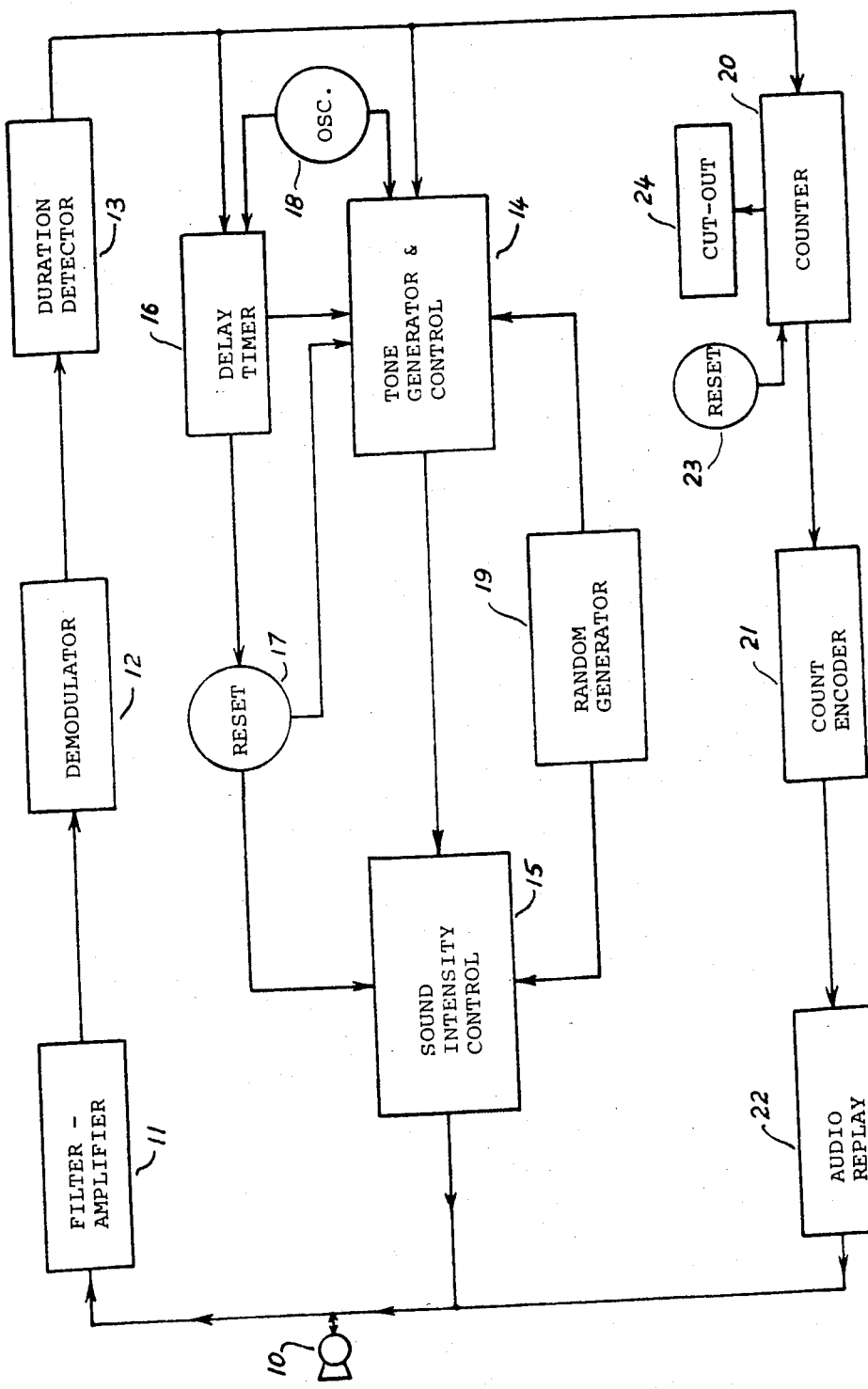
FIG. 1 is a schematic block diagram of a preferred embodiment of the present invention.

As shown in FIG. 1, the anti-snoring device of the preferred embodiment comprises a transducer 10 which is a combined microphone/speaker. Typically, the transducer 10 can be of the electro-magnetic type such as those used in hearing aids, or of piezo-electric ceramic construction which provide a suitable buzzing sound as the audio stimulus. Switching means can be provided in the tone generator and control unit (described herein) to switch between the microphone (receiving) and speaker (transmitting) modes of the transducer 10.

The sounds received by the transducer 10 in its microphone mode are passed to a filter/amplifier 11 which can comprise single or multiple band pass filters to filter the snore frequencies from extraneous noises. For example, the filter/amplifier 11 can include band pass filters to pass frequencies in the ranges of (a) up to 500 HZ and (b) 3 kHZ to 6 kHZ since it has been found that snores typically contain significant audio components in these two ranges.

The filtered snoring frequencies are then passed to a de-modulator or envelope detector 12 which detects the particular amplitude modulation or intonation which characterises a snore. The output of the de-modulator 12 is fed to a duration detector 13 which provides a signal at its output only when the detected "snore" exceeds a preset threshold duration. The duration detector 13 serves to exclude short bursts of sound such as sneezing or tapping of the microphone itself.

The output of the duration detector 13 is connected to a tone generator and control unit 14 which is responsive to the detection of a snore signal to generate an aversive audio stimulus from a signal provided by oscillator 18. In its simplest form, the tone generator unit 14 comprises a transistor switch which is activated by a voltage change at the output of duration detector 13 to switch a audio signal through to the transducer 10. Although the transducer 10 is switched to speaker mode in order to transmit the audio stimulus, it is intermittently switched back to microphone mode to detect snoring sounds.

Figure 2:
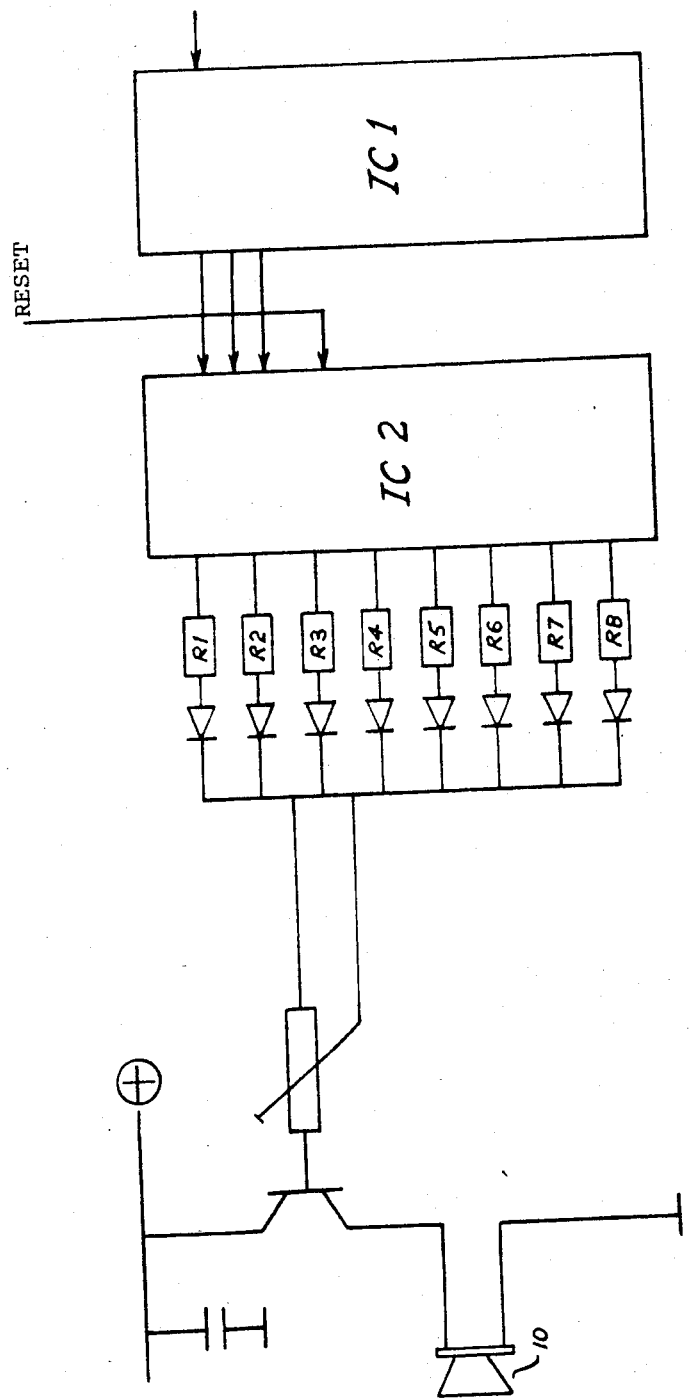
FIG. 2 is a schematic circuit diagram of the sound intensity control of FIG. 1.
Figure 3:
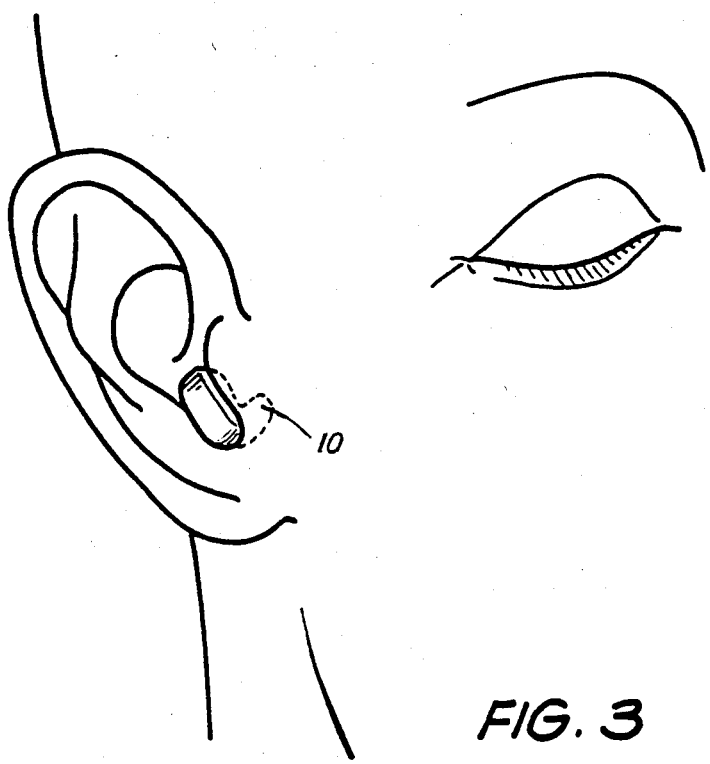
FIG. 3 shows the anti-snoring device mounted in the user's ear.
Figure 4:
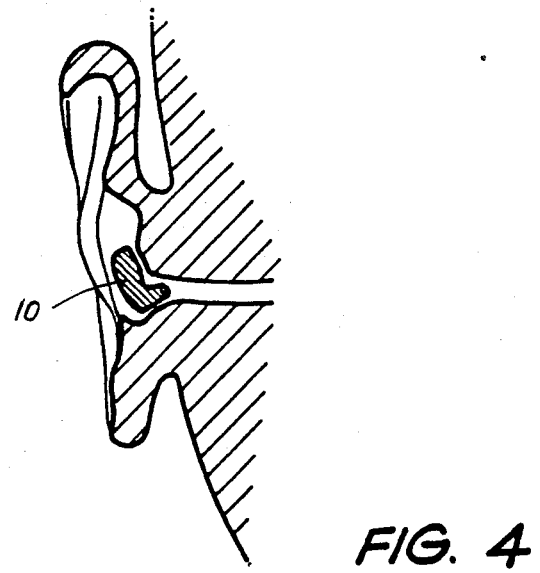
FIG. 4 is a crossectional view showing the anti-snoring device mounted in the user's ear.

The output of the tone generator 14 is passed to the transducer 10 via a sound intensity control unit 15 which varies the amplitude or intensity of the audio stimulus with successive snores in a particular snoring episode. An example of the circuit used to obtain the sound intensity control is shown in FIG. 2. Each detected snore is fed to a counter circuit IC1 which provides a binary output. In the illustrated circuit, a three bit binary output is provided to enable counting up to eight. The three bit binary output is decoded by IC2 into eight discrete voltage levels which control the amplitude of a signal applied to transducer 10. By suitable selection of the resistor values R1 . . . R8, signals of increasing amplitude can be generated with increasing count. When the count reaches eight, the amplitude is maintained at the set maximum level. A similar arrangement can be incorporated in the tone generator and control unit to increase the duration of the audio stimulus over successive snores in the particular snoring episode.

The output of the duration detector 13 is also connected to a delay timer 16 which measures the time delay between detected snores. When the time between snores exceeds a preset value, thereby indicating that a snoring episode has concluded, the delay timer 16 triggers a reset circuit 17 which resets the count in the sound intensity control unit 15 (and the duration control unit 14).

In a particular arrangement, the intensity of the audio signal is arranged to increase with each successive snore, reaching a maximum on the third snore. The audio stimulus is turned off as soon as the snore stops. During the fourth to eighth detected snores, the duration of the audio stimulus is increased with each successive snore, the intensity remaining at the maximum value reached on the third snore. After the eighth snore, the intensity and duration of the audio stimulus remain at the set maximum. Such an arrangement allows for proper behavioural conditioning of the user and minimises habituation. Further, such an arrangement enables the device to apply sufficient, but not excessive, aversivness automatically. It takes into account the fact that the right amount of stimulus will vary from person to person and from time to time. The intensity and duration of the audio stimulus is increased until the required effective level is reached. No volume control is required and there is no need to alter the setting manually to find the optimum setting. As a consequence, the device is simple to use and there is a minimum of disruption to the user.

As a further safeguard against habituation, a random generator 19 can be provided to randomly vary the manner in which the intensity and duration of the audio stimulus increase with successive snores. The introduction of such variability inhibits the process of adpating to the audio stimulus and its pattern of change. It is to be remembered that the device provides subconscious behavioural conditioning and it will not be fully effective if the user becomes habituated to the audio stimulus.

An electronic counter 20 is provided to count the number of detected snores during a particular sleeping period. Since this count is stored electronically, suitable means are provided for "reading" the count. For example, the count can be encoded in count encoder circuit 21, converted to an audio signal in the audio replay circuit 22 and played back through the transducer 10. An exemplary technique involves the binary coding of the count value and the replay of the binary value by frequency shift keying.

A safety cut-out feature 24 can be provided to terminate operation of the device if more than a predetermined number of snores are detected during a particular period of sleep. This obviates unnecessary use of the device and perhaps ear injury when it is apparent that the user is not responding effectively to the device.

The anti-snoring device is miniaturised and encase in a plastic or silicon rubber housing together with its own miniature power supply, such as a silver oxide cell. The housing is moulded to fit comfortably in the user's outer ear, the transducer being arranged thereon so that in use it is positioned at the entrance of the auditory canal. pointing inwards. The circuitry can be fully integrated, or a hybrid integrated circuit can be used.

The foregoing describes only one embodiment of the present invention, and modifications which are obvious to those skilled in the art may be made thereto without departing from the scope of the invention as defined in the following claims.

What I claim is:

1. A compact self-contained electronic anti-snoring device adapted to be worn in or mounted on the outer ear of the user, said device comprising receiving means adapted to fit in the ear and detect snoring sounds via vibrations in the head and the auditory canal of the ear, signal generating means connected to the output of said receiving means and responsive to detection of the snoring sounds for generating an aversive audio signal, and speaker means connected to said signal generating means and adapted to be worn in the outer ear of the user.

2. An anti-snoring device as claimed in claim 1, wherein the receiving means comprises a transducer combining a microphone and said speaker means.

3. An anti-snoring device as claimed in claim 1, wherein said receiving means comprises an audio filter, a demodulator and a snore duration detector connected in series, said snore duration detector providing an output signal to said signal generating means only in response to snoring sounds exceeding a predetermined duration.

4. An anti-snoring device as claimed in claim 1, wherein said signal generating means includes amplitude control means for varying the amplitude of said audio signal with successive detected snoring sounds.

5. An anti-snoring device as claimed in claim 4, wherein said signal generating means further includes duration control means for varying the duration of said audio signal with successive detected snoring sound.

6. An anti-snoring device as claimed in claim 5, further comprising random generating means connected to said amplitude control means and said duration control means for generating controlling signals to vary randomly the manner in which the amplitude and duration of the audio signal vary with successive detected snoring sounds.

7. An anti-snoring device as claimed in claim 5, further comprising timer means connected to the output of said receiving means for measuring the time delay between detected snoring sounds, said timer means providing an output to reset said amplitude control means and said duration control means when the measured delay exceeds a preset value.

8. An anti-snoring device as claimed in claim 1, further comprising means for counting the number of snores detected, encoding means for encoding said number, and playback means for reproducing the encoded number in an audibly detectable form.

9. An anti-snoring device as claimed in claim 5, further comprising cut-out means for terminating the operation of the device when the number of snores detected within a predetermined period exceeds a preset number.

* * * * *